United States Patent [19]

Lozinsky et al.

[11] Patent Number: 4,691,046
[45] Date of Patent: Sep. 1, 1987

[54] BUTANEDIOIC ACID MONO [(2-DIMETHYLAMINO] ETHYL ESTER)SUCCINATE

[75] Inventors: Miron O. Lozinsky, Kiev; Jury G. Bobkov, Moscow; Alla F. Shinanjuk, Kiev; Jury I. Gevaza, Kiev; Leonid N. Markovsky, Kiev; Galina A. Kuznetsova, Moscow; Valentin A. Markin, Moscow; Natalya N. Kleimenova, Moscow; Antonina I. Tentsova, Moscow; Alexandr N. Motalov, Moscow; Sergei B. Seredinin, Moscow; Vladimir F. Katkov; Vasily M. Vinogradov, both of Leningrad; Vladimir I. Kulinsky, Krasnoyarsk, all of U.S.S.R.

[73] Assignees: Institut Organicheskoi Khimii Ordena Lenina I Ordena Druzhby Narodov Akademii Nauk Ukrainskoi SSR, Kiev; Instiut Farmakologii Akademii Meditsinskikh Nauk SSSR, Moscow, both of U.S.S.R.

[21] Appl. No.: 207

[22] Filed: Jan. 2, 1987

[30] Foreign Application Priority Data

Jan. 8, 1986 [SU] U.S.S.R. .............................. 4007025

[51] Int. Cl.$^4$ ............................................. C07C 69/34
[52] U.S. Cl. .................................... 560/196; 560/204
[58] Field of Search ......................... 560/196; 514/547

[56] References Cited

U.S. PATENT DOCUMENTS 3,088,871  5/1963  Pfeiffer ............................... 514/547

Primary Examiner—Werren B. Lone
Assistant Examiner—Vera C. Clarke
Attorney, Agent, or Firm—Burgess, Ryan and Wayne

[57] ABSTRACT

A novel compound, viz, butanedioic acid mono [(2-dimethylamino)ethyl ester] succinate has the following formula:

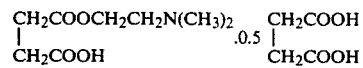

The compound of this invention exhibits adaprogenic and stressoprotective effects.

1 Claim, No Drawings

BUTANEDIOIC ACID MONO [(2-DIMETHYLAMINO] ETHYL ESTER)SUCCINATE

FIELD OF THE INVENTION

The present invention relates to the art of organic chemistry and, more specifically, to a novel chemical compound-butanedioic acid mono[(2-dimethylamino)ethyl ester]succinate exhibiting adaprogenic and stressoprotective effects and useful in experimental biology and medicine as an active principle of a pharmaceutical preparation improving cold-resistance of human beings and farm animals, as well as a stressoprotective agent.

BACKGROUND OF THE INVENTION

Known in the art are structural analogs such as butanedioic acid mono[(2-dimethylamino)ethyl ester] employed in medicine as a stimulant of the central nervous system (cf. U.S. Pat. No. 3,088,071, 1963).

Known in the art is a method for preparing butanedioic acid mono[(2-dimethylamino)ethyl ester] comprising refluxing butanedioic acid anhydride with dimethylaminoethanol in dry acetone on a steam bath; acetone is vaporized, the mixture is cooled and the desired product is isolated therefrom with its subsequent recrystallization from acetone (A. A. Philips, J. Am. Chem. Soc., 1953, 75, 4725-4727). Butanedioic acid mono[(2-dimethylamino)ethyl ester] provides a stimulating effect on the central nervous system (cf. U.S. Pat. No. 3,088,071; 1963).

In the literature data are available regarding the possibility of thiobarbituric acid derivatives of antioxidants such tocopherol as protective agents against an acute cold effect. These data, however, are of merely experimental significance have found no practical use.

The use, in medicine of effective agents possessing the ability of improving the organism's resistance against an acute cold effect and enhance adaptation responses but not been hitherto disclosed in the literature. It is an object of the present invention to provide a method for preparing a novel compound exhibiting adaptogenic and stressoprotective effects.

SUMMARY OF THE INVENTION

It is an object of the present invention to prepare a novel compound exhibiting adaptogenic and stressoprotective effects.

The compound according to the present invention, viz. butanedioic acid mono[(2-dimethylamino)ethyl ester]succinate has the following formula:

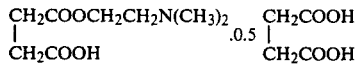

The compound according to the present invention comprises a fine crystalline white powder well soluble in water, sparingly soluble in ethanol and acetone.

The compound according to the present invention exhibits an adaptogenic and stressoprotective effect, has a low toxicity, a high efficiency, provides a stable effect, exerts a positive influence on vitally important systems of the organism, the heart in particular, and can be useful as an active principle improving cold-resistance of human beings and agricultural animals, as well as a stress protective agent.

DETAILED DESCRIPTION OF THE INVENTION

The compound according to the present invention, viz. butanedioic acid mono[(2-dimethylamino)ethyl ester]succinate is prepared by reacting butanedioic acid mono[(2-dimethylamino)ethyl ester] with butanedioic acid in the ratio of 2:1 respectively in an organic solvent such as ethanol. Butanedioic acid mono[(2-dimethylamino)ethyl ester] is prepared by a known procedure through interaction of butanedioic acid anhydride with dimethylaminoethanol in acetone, followed by isolation of the desired product and recrystallization thereof.

The activity of the compound according to the present invention was studied in experiments on animals. The effectivemess of the compound according to the present invention was studied for resistance against an acute cold effect in comparison with conventional preparations such as butanedioic acid mono[(2-dimethylamino)ethyl ester] and sodium succinate.

The experiments were carried out on male mice (tetrahybdrids) with a body mass of 18-20 g which were placed into a cold chamber at a temperature of $-15t$ to $-17°$ C. in separate plastic cages slightly limiting their activity. In experiments with assessment of survival of the animals the duration of the cold effect was 6 hours; by the end of this period all mice of the control group perished. The preparations were administered intraperitoneally 1 hour before the cold effect the control animals were administered with a physiological solution. The test results are shown in Table 1 hereinbelow.

TABLE 1

Effect of preparations on survival of mice on acute cooling

| Nos. | Preparations | Dose, mg/kg | \multicolumn{6}{c}{Survival, %, in the experiment Hours} | | | | | |
|---|---|---|---|---|---|---|---|---|
| | | | 1 | 2 | 3 | 4 | 5 | 6 |
| 1 | Control | — | 100 | 90 | 40 | 10 | 0 | 0 |
| 2 | Butanedioic acid mono [(2-dimethylamino)ethyl ester] | 64 | 100 | 90 | 70 | 50 | 20 | 10 |
| 3 | Compound of this invention | 80 | 100 | 100 | 100 | 90 | 70 | 70 |
| 4 | Sodium succinate | 17 | 100 | 80 | 70 | 40 | 10 | 0 |

A similar effect was observed upon increasing the dose of the compound according to the present invention tol 100 and 200 mg/kg; in doses above 300 mg/kg the protective effect of the compound according to the present invention becomes less pronounced.

An analysis of biochemical shifts characteristic for disorders of metabolism upon acute cold effect was made for the time interval of between the 2-nd and 3-rd hours of the cold effect, since during this interval, as is seen from the data of Table 1, about 50% of mice in the control group died.

Biochemical substrates were identified by conventional procedures: blood glucose—by the o-to-luidine method, liver and myocardiac glycogen—by the procedure suggested by Lo et al., adenine nucleotides of myocardium and creatine phosphate were identified enzymatically; the activity of dehydrogenases was evaluated using cryostatic sections of myocardium by generally accepted histochemical methods (activities in the control and against the background of the compound according to the present invention were compared).

The preparations were administered one hour before the standard low-temperature treatment ($-14°$ C.) in doses of 80 mg/kg of the compound according to the present invention and 64 mg/kg of the prior art compound-butanedioic acid mono[(2-dimethylamino)-ethyl ester]. The test results are shown in Table 2 hereinbelow.

TABLE 2

| Nos 1 | Biochemical substrates 2 | Control 3 | Butanedioic acid mono-[(2-dimethyl-amino)-ethyl ester] 4 | Compound 5 |
|---|---|---|---|---|
| Variation of biochemical characteristics in mice upon preset (2.5 hours) low-temperature treatment against the background of preparations | | | | |
| 1 | Blood glucose (mg. %) 79 ± 3 (intact) animals | 42 ± 4 | 64 ± 2 | 80 ± 4$^x$ |
| 2 | Heart glucogen (mg/g) 3.6 ± 0.2 | 1.8 ± 0.1 | 1.9 ± 0.1 | 2.2 ± 0.1$^x$ |
| 3 | Liver glycogen (mg/kg) 35.2 ± 4.5 | 8.1 ± 0.6 | 6.7 ± 0.8 | 9.8 ± 1.2 |
| 4 | Adenosine triphosphoric acid (μm/g) 2.2 ± 0.3 | 1.5 ± 0.1 | — | 1.9 ± 0.2$^x$ |
| 5 | Adenosine diphosphate (μm/g), 0.78 ± 0.03 | 0.49 ± 0.02 | — | 0.86 ± 0.04$^x$ |
| 6 | Adenosine monophosphate (μm/g), 0.51 ± 0.03 | 0.45 ± 0.01 | — | 0.32 ± 0.02$^x$ |
| 7 | Creatine phosphate (μm/g), 3.7 ± 0.3 | 1.2 ± 0.08 | 1.4 ± 0.04 | 2.3 ± 0.1$^x$ |
| Activity of dehydrogenases in myocardium (in relative units) | | | | |
| 8 | Succinatedehydrogenase | 72.3 ± 1.6 | 75.6 ± 2.4 | 90.2 ± 1.8$^x$ |
| 9 | Isocitratedehydrogenase | 49.5 ± 1.2 | 58.2 ± 1.4 | 60.4 ± 1.6$^x$ |
| 10 | Glutamatedehydrogenase | 68.8 ± 1.5 | 72.4 ± 0.6 | 78.3 ± 1.7$^x$ |
| 11 | Pyruvatedehydrogenase | 56.6 ± 1.1 | 62.6 ± 3.5 | 68.9 ± 1.3$^x$ |
| 12 | NADH$_2$—dehydrogenase | 69.8 ± 1.5 | 70.8 ± 2.7 | 73.4 ± 2.0 |
| 13 | NAD-Ph—H$_2$—dehydrogenase | 72.1 ± 1.4 | 76.4 ± 2.7 | 85.9 ± 1.7 |
| 14 | Glucose-6-phosphatedehydrogenase | 57.3 ± 1.3 | 60.2 ± 1.4 | 67.4 ± 1.5$^x$ |

Note:
The sign $^x$ denotes significant differences in respect of the control group of animals.

As follows from the data shown in the above Table 2, a preliminary administration of the compound according to the present invention contributes to a longer retention of the content of glucose and glycogen in the myocardium, to a greater content of adenyl nucleotides and creatine phosphate in the myocardium and to a substantially higher activity of the key enzymes of Krebs' cycle (dehydrogenase succinate, pyruvatedehydrogenase, isocitratedehydrogenase) in the myocardium. It should be noted that in individual series of experiments the activity of these enzymes against the background of the preparation was even higher, though the general orientation of the effect was the same.

The thus-obtained data suggest that a longer lifespan against the background of the compound according to the present invention is caused by a better preservation of energy substrates in the myocardium and a higher level of metabolism. Eventually, this very factor can be of vital importance for survival, since it is known that one of the main reasons of death upon acute overchilling resides in heart insufficiency.

Under real conditions long-time residence under a low-temperature effect is alway accompanied by the development of adaptation resulting in an increased resistance of the organism to the effect of cold. Physiological or biological shifts can serve as adaptation criteria. However, the most clear-cut feature of adaptation is the raise of survival upon the effect of the extreme factor.

To elucidate the effect of the compound according to the present invention on the adaptation phenomenon, experiments on male mice with a body mass of 18-20 g were carried out in conformity with the Le Blanc procedure according to which the mice were placed into a cold chamber (at $-17°$ C.) for 10 minutes ever hour over the period of 9-10 hours. After one day the maximum lifespan of the mice at $-17°$ C. was assessed along with the content of glucose in blood and of glycogen in organs upon a predetermined cold treatment (2.5 hours a $-14°$ C.). The compound according to the present invention and butanedioic acid mono[(2-dimethylamino)-ethyl ester] (in doses of 80 and 64 mg/kg respectively) were introduced immediately after a series of short-time cold effects. In a number of experiments the compound according to the present invention was administered 1 hour prior to the testing (2.5 h) cold effect. The test results are shown in the following Tables 3 and 4.

As follows from these data, the administration of the compound according to the present invention considerably enhances the adaptation effect which is displayed in an extended lifespan of the mice prior to freezing and in a considerably higher preservation of the level of glucose in blood and of glycogen in organs upon a short-time (2.5 h) temperature effect. Taking into consideration the short duration of the preliminary adaptation, it can be assumed that the compound according to the present invention may find practical application in this respect.

TABLE 3

Maximum duration of mice lifespan upon testing cold treatment

| Mode of treatment | Number of animals | Lifespan in hours (at $-17°$ C.) |
|---|---|---|
| Intact animals | 12 | 3.4 ± 0.4 |
| Preliminary adaptation | 12 | 6.0 ± 0.3 |
| Preliminary adaptation + the compound of the present invention (80 mg/kg) | 12 | 10.3 ± 0.6 |

TABLE 3-continued

Maximum duration of mice lifespan upon testing cold treatment

| Mode of treatment | Number of animals | Lifespan in hours (at −17° C.) |
|---|---|---|
| Preliminary adaptation + butanedioic acid mono-[(2-dimethylamino)-ethyl ester] | 12 | 6.2 ± 0.4 |
| Compound of the present invention | 12 | 7.8 ± 0.3 |

TABLE 4

Variation of biochemical characteristics upon predetermined (2.5 h) cold treatment

| Nos. 1 | Mode of treatment 2 | Blood glucose, mg. % 3 | Glycogen, mg/g heart 4 | Glycogen, mg/g liver 5 |
|---|---|---|---|---|
| 1 | Intact animals (residence at +20° C.) | 79 ± 4 | 3.6 ± 0.4 | 35 ± 2.1 |
| 2 | Control (2.5 hours at −14° C.) | 37 ± 6 | 1.7 ± 0.2 | 6.7 ± 0.4 |
| 3 | Adaptation | 60 ± 4$^x$ | 2.4 ± 0.3$^x$ | 20.4 ± 1.6$^x$ |
| 4 | Adaptation + the compound of this invention (immediately after adaptation) | 88 ± 2$^x$ | 2.9 ± 0.2$^x$ | 18.2 ± 2.1$^x$ |
| 5 | Adaptation + butanedioic acid mono (2-dimethylamino)-ethyl ester] (immediately after adaptation | 75 ± 4$^x$ | 2.4 ± 0.2$^x$ | 10.2 ± 2.7$^x$ |
| 6 | Adaptation + the compound of this invention (1 hour before the testing effect) | 78 ± 6$^x$ | 2.6 ± 0.4$^x$ | 11.7 ± 2.4$^x$ |
| 7 | The compound of this invention (1 hour prior to the testing effect) | 59 ± 2.6$^x$ | 2.2 ± 3.4 | 7.1 ± 2.6 |

Note:
The symbol $^x$ stands for the certainty of differences with regard to the control group ($P < 0.05$ by Student's test).

In evaluation of the stresso-protective activity of the compound according to the present invention as a model use was made of a procedure of depriving rats of sleep, meals and water in a slowly rotating drum (at the speed of 0.2 km/h).

The experiments were carried out on 42 nondescript male rats. In parallel experiments the antistress activity of butanedioic acid mono[(2-dimethylamino)ethyl ester] was studied; as the reference prepartion use was made of the prior art tranquilizer—diazepam which was used in the experiments for this very indication.

4 groups of animals were tested in parallel. Groups I and II were placed for 48 hours into a slowly rotating drum, groups III and IV were under normal conditions and were deprived only of meals and water. The compound according to the present invention and butanedioic acid mono[(2-dimethylamino)ethyl ester] were administered intraperitoneally in the dose of 10 mg/kg four times (2 times a day) in the volume of 2.5 ml/kg under the conditions of motion stress (Group I of the animals) and under normal conditions (Group III of animals). The control animals—Group II (active control) and Group IV (passive control) were given a physiological solution. The efficiency of the compound according to the present invention, of butanedioic acid mono[(2-dimethylamino)ethyl ester] and of diazepam was estimated on the basis of a set of characteristics showing the functional activity of the central nervous system, physical fitness and development of basic symptoms of the stress-syndrome.

The residence of control rats in a slowly-rotating drum over 48 hours results in a noticeable deterioration of all the studied characteristics, especially those of higher nervous activity (learning) and development of stress-syndrome. The state of control animals was characterized by lowering of the overall behavioural activity as determined by the "open-field" test (37±15%) with reference to the passive control level, by a reduction in the speed of development of a conventional avoiding response in an aqueous labyrinth (58±15%), by an increase in the number of mistakes during the teaching time (175±25%), lowering of the ultimate physical endurance as determined by the swimming-with-load test (the load is equal to 10% by mass of the body (70±17%), adrenal hypertrophy (146±16%), thymus atrophy (49±9%) and formation of ulcers on the stomach mucous membrane (5.25±1.0%).

The test results are shown in Table 5 hereinbelow.

TABLE 5

Effect of the tested compounds on the characteristics of functional activity of the central nervous system, physical endurance and symptoms of stress-syndrome under conditions of motion stress for 48 hours

| | Group of animals after 48 hours' treatment | | | |
|---|---|---|---|---|
| Test parameters 1 | Control 2 | Compound of the present invention 3 | Butane dioic acid mono [(2-dimethyl-amino)-ethyl ester] 4 | Diazepam 5 |
| Number of attempts till reaching the learning criterion (water labyrinth) | 4.75± ±0.5 | 2.75± ±0.25$^x$ | 4.10± ±0.38 | 7.25± ±0.80$^x$ |
| Duration of swimming (seconds) | 244± ±26 | 499± ±98$^x$ | 325± ±15$^x$ | 210± ±45 |
| Number of ulcers on the stomach mucous membrane | 5.25± ±1.0 | 2.5± ±0.8$^x$ | 4.2± ±0.6 | 1.0± ±0.5$^x$ |
| Weight coefficient of adrenal glands (g/kg of the initial body mass) | 1.246 ± 0.028 | 1.83± +0.016$^x$ | 1.42± ±0.08 | 1.010± ±0.015 |
| Weight coefficient of thymus (g/kg of the initial body mass) | 0.95 ± 0.18 | 1.25± ±0.95 | 1.08± ±0.14 | 2.26± ±0.15 |

The study of the compound according to the present invention under the motion stress conditions revealed its pronounced protective effect in respect of both the characteristics functional activity of the central nervous system and the stress-syndrome. The use of the compound according to the present invention increased the total behavioural activity (85±10%), physical endurance (143±28%), lowered the formation of ulcers on the stomach mucous membrane (4.8±1.5%) and, what is especially important, fully protected the higher nervous activity under these conditions (100±9%).

A comparison of the effect produced by the compound according to the present invention with that obtained from administration of butanedioic acid mono[(2-dimethylamino) ethyl ester] has revealed a similar directedness of the stresso-protective activity of the latter, though this effect is far less pronounced. A comparison of the cited data shows that the compound according to the present invention has distinct advantages over diazepam: certainly and substantially higher general behavioural activity against the background of the compound according to the present invention, the processes of teaching and learning of a of a habit are disturbed to a far lesser extent, the physical endurance against the background of a stress effect is much higher.

Against the background of diazepam the formation of ulcers is prevented to a greater extent, the weight coefficient of thymus is decreased to a lesser extent, though hypertrophy of adrenal glands against the background of diazepam is higher than in the case of the compound according to the present invention.

On the basis of the above data it can be assumed that the compound according to the present invention is useful as a stressoprotective agent in situations which are accompanied by impaired operators performance.

The compound according to the present invention has a low toxicity, its $LD_{50}$ in mice upon intraperitoneal administration is 3,040 mg/kg.

The following example illustrating the preparation of the compound according to the present invention is given hereinbelow for a better understanding thereof.

EXAMPLE 1

18.9 g (0.1 mole) of butanedioic acid mono[(2-dimethylamino)ethyl ester] are dissolved upon heating in 100 ml of ethanol. The resulting solution is added with a solution of 5.9 g (0.05 mole) of succinic acid in 50 ml of ethanol. The reaction mixture is allowed to stand for 12 hours at the temperature of 20° C., the formed white fine crystalline precipitate is filtered-off and recrystallized from ethanol.

22.0 g (84%) of butanedioic acid mono[(2-dimethylamino)ethyl ester]succinate are obtained. M.p. 134°–136° C.

Found, %: C 48.18, H 7.47, N 5.71. $C_{20}H_{36}N_2O_{12}$ Calculated, %: C 48.38; H 7.25, N 5.64.

$R_f=0.37$ (Silufol UV-254, n-butanol—acetic acid—water, 5:2:4).

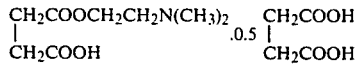

What is claimed is:

1. Butanedioic acid mono[(2-dimethylamino)ethyl ester]succinate of the formula: